United States Patent [19]

Wang et al.

[11] Patent Number: 6,113,852
[45] Date of Patent: Sep. 5, 2000

[54] METHOD OF PREPARING A STERILE MEDICAL ARTICLE

[75] Inventors: Qi Wang; Sandor Nagy, both of Grand Island; Mingzhu Xu, Amherst, all of N.Y.

[73] Assignee: Occidental Chemical Corporation, Dallas, Tex.

[21] Appl. No.: 09/135,120

[22] Filed: Aug. 17, 1998

[51] Int. Cl.$^7$ ...................................................... A61L 2/08
[52] U.S. Cl. .............................................................. 422/22
[58] Field of Search ................................ 422/22; 524/108, 524/357, 396, 567; 556/40; 568/494

[56] References Cited

U.S. PATENT DOCUMENTS 3,453,300  7/1969  Backus et al. .
3,474,464  10/1969  Matthews et al. .
3,492,267  1/1970  Wood .

FOREIGN PATENT DOCUMENTS 57003653  of 0000  Japan .

OTHER PUBLICATIONS

An Article by Douglas W. Luther et al., titled Improving Gamma Radiation Resistance: Medical Grade, Flexible Clear PVC Compounds, Sep. 1996, vol. 2 No. 3.

Article by K.Z. Hong, "Poly(Vinyl Chloride) in Medical Device and Packaging Applications" Sep. 1996 vol. 2, No. 3—pp. 193 to 197.

Article by Joseph W Burley, "New Organic Costabilizers for the Stabilization of PVC" Sep. 1997, vol. 3, No. 3 pp. 205 to 209.

Osawa, Zenjiro et al, "Effect of various metal acetylacetonates on the photodegradation of poly)vinyl chloride)", Polym. Photochem. (1982), 2(6), p. 447–55.

*Primary Examiner*—Elizabeth McKane
*Attorney, Agent, or Firm*—Anne E. Brookes; Richard D. Fuerle

[57] ABSTRACT

Disclosed is a method of preparing a sterile medical article. A poly(vinyl chloride) or polyvinylidene chloride polymer is produced that contains about 0.001 to about 5 wt % of a metal complex having at least one anionic ligand that has at least one resonance structure in which the charge is localized on a carbon atom. A medical article is fabricated from the chlorinated polymer and the medical article is exposed to gamma radiation.

20 Claims, No Drawings

METHOD OF PREPARING A STERILE MEDICAL ARTICLE

BACKGROUND OF THE INVENTION

This invention relates to the preparation of sterile medical articles by producing a chlorinated polymer that contains a metal complex, fabricating the medical article from the chlorinated polymer and exposing the medical article to gamma radiation. In particular, the metal complex used has at least one anionic ligand that has the least one resonance structure in which the charge is localized on a carbon atom.

Poly(vinyl chloride) (PVC) has properties that make it desirable for use as medical devices and as packaging for medical applications. Articles that are used in the medical field have to be sterilized before they are used. Gamma radiation is often used for this purpose. It has been found, however, that gamma radiation causes PVC to become yellow and medical articles that have turned yellow may be rejected as being of inferior quality. Articles made of PVC that are re-used and sterilized after each use are especially likely to turn yellow.

A variety of substances have been added to PVC to stabilize it from gamma radiation and prevent yellowing, including organic Ca\Zn soap blends (JP 57,003,653), organo tin compounds (JP 02189352, JP 08073619, and EP 83112278), and sulfur compounds (JP 08151495, 07102142, and 01278551).

SUMMARY OF THE INVENTION

We have discovered that the addition of certain metal complexes to PVC and polyvinylidene chloride stabilize the polymers against gamma radiation. The metal complexes can be easily added to the polymers during polymerization or processing so that no additional procedural steps are required. The medical articles can be sterilized with gamma radiation without significant yellowing.

DESCRIPTION OF THE PREFERRED EMBODIMENTS

In the method of this invention, a sterile medical article is prepared by first producing a chlorinated polymer with a metal complex additive. The chlorinated polymer may be either PVC or polyvinylidene chloride. The metal complex can be added to the polymer at any stage, such as, for example, to the monomer, to the partially polymerized monomer, during the drying of the polymer, or during processing of the polymer into the medical article. However, it is preferably added at the earliest possible stage after the monomer has at least partially polymerized in order to avoid any extra procedural steps and to ensure its complete incorporation into the polymer.

The metal complex that is added to the polymer to stabilize it against gamma radiation contains at least one anionic ligand that has at least one resonance structure in which the charge is localized on a carbon atom. That is, the anionic ligand resonates between two structures and, in at least one of those structures, the negative charge is localized on a carbon atom. For example, if the anionic ligand is acetylacetonate the following two structures resonate, where the negative charge is on the carbon atom in one of the two structures.

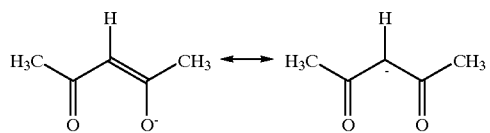

Generally, the metal complex can have the general formula

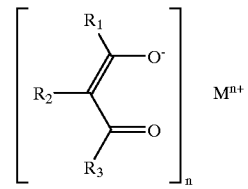

where M is a metal, $R_1$, $R_2$, and $R_3$ are each independently selected from R, OR, SR, and N(R)$_2$, R is hydrogen, alkyl from $C_1$ to $C_{12}$, or aryl from $C_6$ to $C_{18}$, and n is the valence of M. Preferably, $R_1$ and $R_3$ are each independently selected from alkyl and alkoxide from $C_1$ to $C_8$ and are the same as that simplifies synthesis of the complex. Preferably, $R_2$ is hydrogen as those compounds are more readily available. Examples of metals that can be used include calcium, barium, zinc, cadmium, lead, tin, and aluminum. Divalent metals (n=2) are preferred as the Lewis acidity of those complexes is in the desirable range and adjustments to acidity can be avoided. Zinc is the preferred metal as zinc complexes have less toxicity and are less expensive. Examples of more preferred zinc complexes include

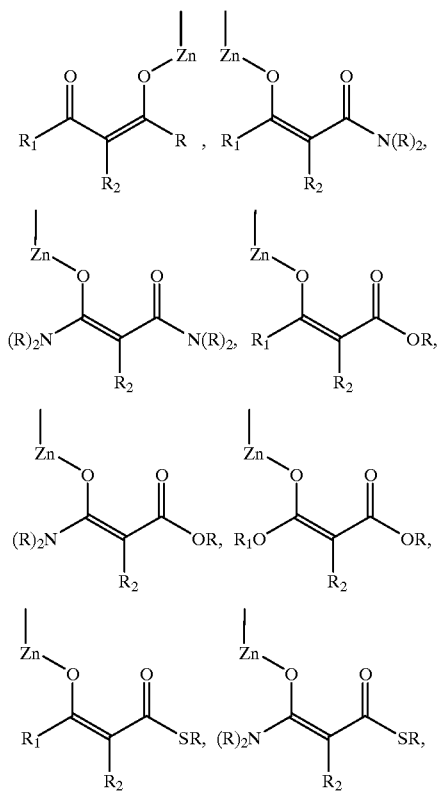

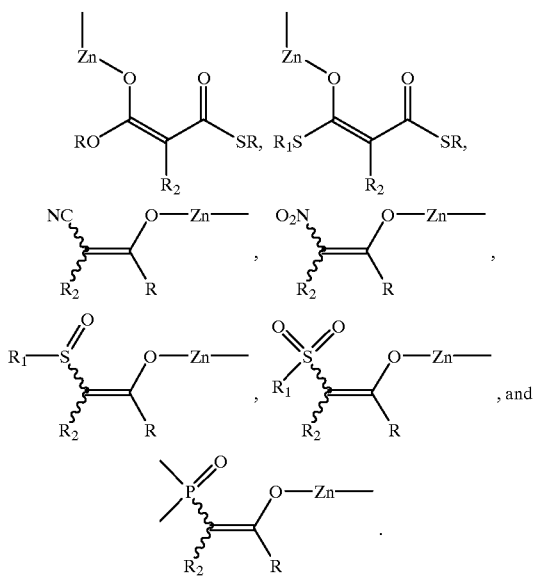

The amount of metal complex added can be about 0.0001 wt % to about 5 wt %, based on the weight of the polymer; the preferred range is about 0.001 to about 0.5 wt %.

In addition, plasticizers, heat stabilizers, epoxidized soybean oil, lubricants, and other additives can be mixed in with the PVC as is well known in the art.

The following examples further illustrate this invention.

EXAMPLES 1 to 5

To mixtures of 150.00 g PVC (sold by Occidental Chemical Corp. as "Oxy 240"), 0.30 g stearic acid, 0.23 g of a soap thermal stabilizer sold by Witco as "Mark 152 S," 97.50 g dioctyl phthalate, and 15.00 g epoxidized soybean oil sold by Witco as "Drapex 6.8" was added various amounts of different zinc salts of β-biscarbonyl compounds. The mixtures were thoroughly blended and hot milled at 300° F. (149° C.) for 5 minutes. The resulting PVC sheets were pressed at 330° F. (166°C.) and cut into 4"×3"×¼" (10 cm×8 cm×0.6 cm) plaques. The plaques were divided into two smaller pieces. One piece was saved for the purpose of comparison and the other one was subjected to 5.0 Mrad of γ radiation at 50 kGy. The irradiated piece was again divided into two pieces and one piece was oven aged at 50° C. for 48 hours. All three pieces were measured for yellowness index with a Mascbeth 2020 Plus Color Eye Spectrometer. The control materials were similarly prepared, but without a zinc complex of a β-biscarbonyl compound. The following table gives the results:

| | | Yellowness | |
|---|---|---|---|
| Example | Metal Complex | With Metal Complex | Without Metal Complex |
| 1 | 0.35 g | Initial 11.3 | 12.4 |
| | Zn acetylacetonate | After Y 29.4 | 45.0 |
| | | Aged 37.2 | 72.0 |
| 2 | 0.60 g | Initial 21.6 | 19.8 |
| | Zn acetylacetonate | After Y 34.1 | 52.8 |
| | | Aged 38.8 | 73.3 |

| | | Yellowness | |
|---|---|---|---|
| Example | Metal Complex | With Metal Complex | Without Metal Complex |
| 3 | 0.91 g | Initial 34.5 | 19.8 |
| | Zn acetylacetonate | After Y 35.1 | 52.8 |
| | | Aged 37.4 | 73.3 |
| 4 | 0.35 g | Initial 16.4 | 12.4 |
| | Zn bis(2,2,6,6-tetramethyl- | After Y 39.5 | 45.0 |
| | 3,5-heptanedionate | Aged 57.7 | 72.0 |
| 5 | 0.31 g | Initial 11.6 | 12.4 |
| | Zn hexafluoroacetylacetonate | After Y 36.8 | 45.0 |
| | | Aged 55.0 | 72.0 |

The table shows that the PVC that contain zinc salts of β-biscarbonyl compounds had significantly less discoloration after γ radiation compared with the control samples, which did not contain those compounds.

EXAMPLES 6 to 9

Example 1 was repeated using various zinc salts as β radiation stabilizers or the same molar equivalent amount of the corresponding ketone (see JP 02263853). The following table gives the stabilizers tested and the results:

| | | | Yellowness | |
|---|---|---|---|---|
| Example | Zinc Salt (g) Ketone | Initial | After γ Rays | After Aging |
| 6 | Zinc acetylacetonate (0.40) | 19.1 | 38.6 | 45.9 |
| | 2,4-pentanedione | 16.9 | 55.8 | 76.3 |
| 7 | Zinc 1-benzoylacetonate (0.59) | 18.9 | 39.4 | 44.9 |
| | 1-benzoylacetone | 15.6 | 50.9 | 72.6 |
| 8 | Zinc(methoxyethoxy)carbonyl acetonate (0.58) | 19.0 | 40.6 | 49.1 |
| | 2-methoxyethoxy acetoacetate | 18.0 | 54.0 | 73.3 |
| 9 | Zinc 3-(2'-ethylcarboxyethyl)-2,4-petanedionate (0.70) | 21.9 | 45.0 | 52.9 |
| | Ethyl 4-acetyl-5-oxohexanoate | 17.1 | 49.6 | 61.5 |

The above table shows that the zinc salts are more effective in reducing yellowness than the corresponding ketones.

We claim:

1. A method of preparing a sterile medical article comprising (A) producing a chlorinated polymer selected from polyvinyl chloride and polyvinylidene chloride that contains about 0.0001 to about 5 wt % of zinc complex having at least one anionic ligand that has at least one resonance structure in which the charge is localized on a carbon atom;

(B) fabricating said medical article from said chlorinated polymer; and (C) sterilizing said medical article with gamma radiation.

2. A method according to claim 1 wherein said zinc complex has the general formula

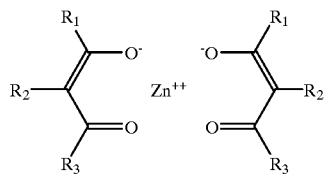

wherein $R_1$, $R_2$, and $R_3$ are each independently selected from R, OR, SR, and $N(R)_2$, and R is hydrogen, alkyl from $C_1$ to $C_{12}$, or aryl from $C_6$ to $C_{18}$.

3. A method according to claim 2 wherein $R_2$ is hydrogen.

4. A method according to claim 2 wherein metal complex has the formula

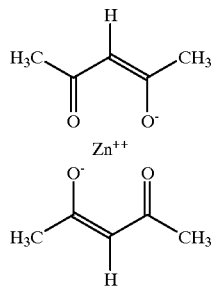

5. A method according to claim 1 wherein $R_1$ and $R_3$ are each independently selected from alkyl and alkoxide from $C_1$ to $C_8$.

6. A method according to claim 1 wherein said chlorinated polymer is poly(vinyl chloride).

7. A method according to claim 1 wherein said chlorinated polymer is polyvinylidene chloride.

8. A sterile medical article prepared according to the method of claim 1.

9. A method according to claim 1 wherein said zinc complex is selected from the group consisting of

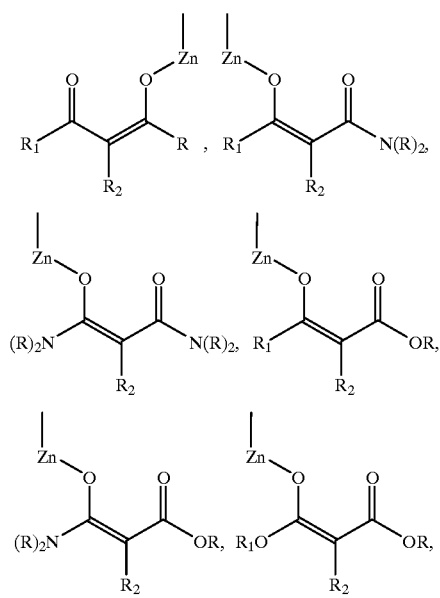

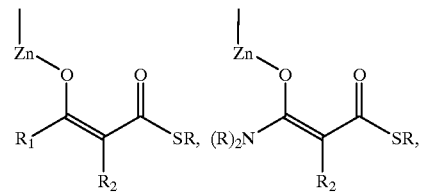

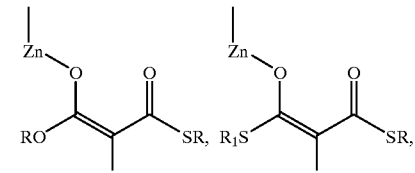

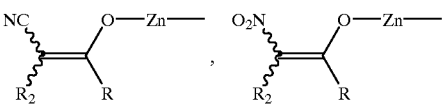

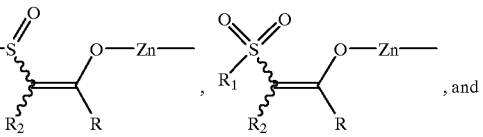

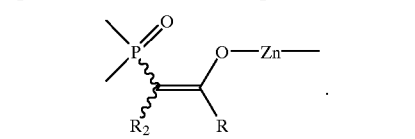

, and

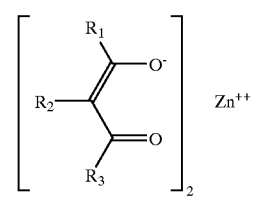

where $R_1$, $R_2$, and $R_3$ are each independently selected from the group consisting of R, OR, SR, and $N(R)_2$, and R is hydrogen, alkyl from $C_1$ to $C_{12}$, or aryl from $C_6$ to $C_{18}$.

10. A method of preparing a sterile medical article comprising (A) making poly(vinyl chloride) that contains about 0.001 to about 0.5 wt % of a zinc complex having the general formula $$\left[ \begin{array}{c} R_1 \\ R_2 \\ R_3 \end{array} \right]_2 Zn^{++}$$

where $R_1$, $R_2$, and $R_3$ are each independently selected from R, OR, SR, and $N(R)_2$, and R is hydrogen, alkyl from $C_1$ to $C_{12}$, or aryl from $C_6$ to $C_{18}$;

(B) fabricating said medical article from said poly(vinyl chloride); and (C) repeatedly sterilizing said medical article with gamma radiation.

11. A method according to claim 10 wherein said zinc complex has the formula

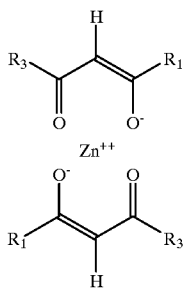

where $R_1$ and $R_3$ are each independently selected from alkyl and alkoxide from $C_1$ to $C_8$.

12. A method according to claim 11 wherein $R_1$ and $R_3$ are $CH_3$.

13. A sterile medical article prepared according to the method of claim 10.

14. A method according to claim 10 wherein said zinc complex is selected from the group consisting of

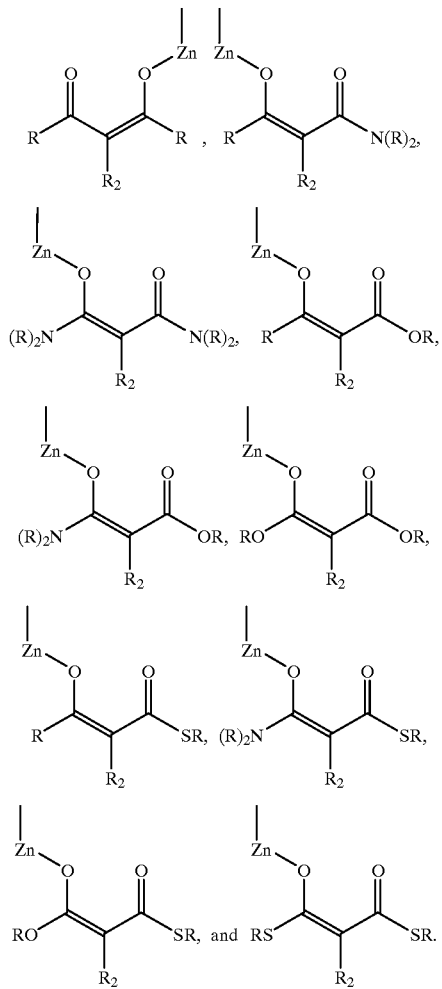

15. A method according to claim 14 wherein said zinc complex has the formula

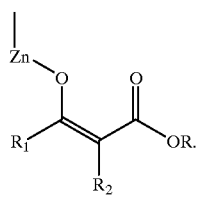

16. A method according to claim 14 wherein said zinc complex has the formula

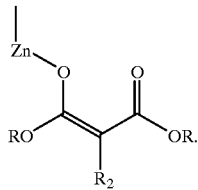

17. A method according to claim 14 wherein said zinc complex has the formula

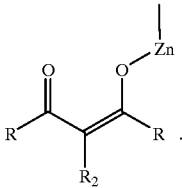

18. A method of preparing a sterile medical article comprising
(A) making poly(vinyl chloride) that contains about 0.001 to about 0.5 wt % of a zinc complex having the general formula

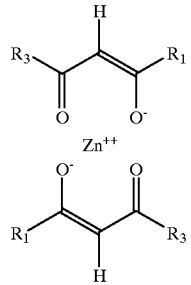

where $R_1$ and $R_3$ are each independently selected from alkyl and alkoxide from $C_1$ to $C_8$;
(B) fabricating said medical article from said poly(vinyl chloride); and
(C) repeatedly sterilizing said medical article with gamma radiation.

19. A method according to claim 18 wherein $R_1$ and $R_3$ are methyl.

20. A sterile medical article prepared according to the method of claim 18.

* * * * *